(12) United States Patent
Thao et al.

(10) Patent No.: US 10,799,176 B2
(45) Date of Patent: Oct. 13, 2020

(54) SYSTEMS AND METHODS FOR ASSESSING TISSUE CONTACT

(71) Applicant: St. Jude Medical, Atrial Fibrillation Division, Inc., St. Paul, MN (US)

(72) Inventors: Riki Thao, Brooklyn Park, MN (US); Saurav Paul, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1225 days.

(21) Appl. No.: 14/151,273

(22) Filed: Jan. 9, 2014

(65) Prior Publication Data

US 2014/0228713 A1 Aug. 14, 2014

Related U.S. Application Data

(63) Continuation of application No. 11/617,364, filed on Dec. 28, 2006, now Pat. No. 8,672,936, which is a
(Continued)

(51) Int. Cl.
*A61B 18/14* (2006.01)
*A61B 5/00* (2006.01)
(Continued)

(52) U.S. Cl.
CPC .......... *A61B 5/4848* (2013.01); *A61B 18/14* (2013.01); *A61B 18/1492* (2013.01);
(Continued)

(58) Field of Classification Search
CPC .............. A61B 18/14; A61B 18/1492; A61B 2018/00351; A61B 2018/00577;
(Continued)

(56) References Cited

U.S. PATENT DOCUMENTS

| 4,600,017 A | 7/1986 | Schroeppel |
| 4,682,596 A | 7/1987 | Bales |

(Continued)

FOREIGN PATENT DOCUMENTS

| EP | 1491139 | 12/2004 |
| WO | 1995/10978 | 4/1995 |

(Continued)

OTHER PUBLICATIONS

Author: , Title: Fiber Optic Interferometer Fabry-Perot Citation: http://physics.nad.ru/Physics/English/ifp_txt.htm Reference pp. 1-5 Publication Date: Oct. 15, 2007.

(Continued)

*Primary Examiner* — Michael F Peffley
*Assistant Examiner* — Amanda L Zink
(74) *Attorney, Agent, or Firm* — Dykema Gossett PLLC

(57) ABSTRACT

Systems and methods are disclosed for assessing tissue contact, e.g., for mapping, tissue ablation, or other procedures. An exemplary tissue contact sensing system comprises a flexible tip device. At least one piezoelectric sensor is housed within the flexible tip device. The at least one piezoelectric sensor is responsive to contact stress of the flexible tip device by generating electrical signals corresponding to the amount of contact stress. An output device is electrically connected to the at least one piezoelectric sensor. The output device receives the electrical signals for assessing tissue contact by the flexible tip device. Methods for assembling and using the flexible tip device are also disclosed.

20 Claims, 11 Drawing Sheets

Related U.S. Application Data continuation-in-part of application No. 11/553,965, filed on Oct. 27, 2006, now Pat. No. 8,021,361, which is a continuation-in-part of application No. 11/549,100, filed on Oct. 12, 2006, now Pat. No. 8,679,109.

(60) Provisional application No. 60/730,634, filed on Oct. 27, 2005, provisional application No. 60/727,164, filed on Oct. 13, 2005.

(51) Int. Cl.
*A61B 18/00* (2006.01)
*A61B 90/00* (2016.01)

(52) U.S. Cl.
CPC ............. *A61B 2018/0066* (2013.01); *A61B 2018/00351* (2013.01); *A61B 2018/00577* (2013.01); *A61B 2018/00839* (2013.01); *A61B 2018/143* (2013.01); *A61B 2090/065* (2016.02)

(58) Field of Classification Search
CPC .. A61B 2018/0066; A61B 2018/00839; A61B 2018/143; A61B 2090/065; A61B 5/4848
See application file for complete search history.

(56) References Cited

U.S. PATENT DOCUMENTS

| | | | |
|---|---|---|---|
| 4,799,495 A | | 1/1989 | Hawkins |
| 4,911,174 A | | 3/1990 | Pederson |
| 4,976,711 A | | 12/1990 | Parins |
| 4,991,588 A | | 2/1991 | Pflueger |
| 5,028,394 A | | 7/1991 | Lowell, Jr. |
| 5,176,677 A | * | 1/1993 | Wuchinich ............ A61F 2/46 604/22 |
| 5,327,905 A | | 7/1994 | Avitall |
| 5,341,807 A | | 8/1994 | Nardella |
| 5,354,279 A | | 10/1994 | Hofling |
| 5,372,603 A | | 12/1994 | Acker |
| 5,396,887 A | * | 3/1995 | Imran ............ A61B 5/0422 600/374 |
| 5,405,346 A | | 4/1995 | Grundy |
| 5,447,529 A | | 9/1995 | Marchlinski |
| 5,536,245 A | | 7/1996 | Dahlbeck |
| 5,545,161 A | | 8/1996 | Imran |
| 5,643,197 A | | 7/1997 | Brucker |
| 5,645,065 A | * | 7/1997 | Shapiro ............ A61B 5/06 128/899 |
| 5,697,925 A | | 12/1997 | Taylor |
| 5,782,828 A | | 7/1998 | Chen |
| 5,836,990 A | | 11/1998 | Li |
| 5,865,801 A | * | 2/1999 | Houser ............ A61B 5/036 600/488 |
| 5,868,737 A | | 2/1999 | Taylor |
| 5,893,848 A | | 4/1999 | Negus |
| 5,895,355 A | | 4/1999 | Schaer |
| 5,947,905 A | | 9/1999 | Hadjicostis |
| 6,013,074 A | | 1/2000 | Taylor |
| 6,039,731 A | | 3/2000 | Taylor |
| 6,063,022 A | * | 5/2000 | Ben-Haim ............ A61B 34/20 600/41 |
| 6,066,139 A | | 5/2000 | Ryan |
| 6,078,830 A | | 6/2000 | Levin |
| 6,113,592 A | | 9/2000 | Taylor |
| 6,113,593 A | | 9/2000 | Tu |
| 6,127,672 A | | 10/2000 | Danisch |
| 6,171,304 B1 | | 1/2001 | Netherly |
| 6,210,406 B1 | | 4/2001 | Webster |
| 6,217,573 B1 | | 4/2001 | Webster |
| 6,217,574 B1 | | 4/2001 | Webster |
| 6,241,724 B1 | * | 6/2001 | Fleischman ......... A61B 18/1492 600/374 |
| 6,246,898 B1 | | 6/2001 | Vesely |
| 6,264,653 B1 | | 7/2001 | Falwell |
| 6,272,371 B1 | | 8/2001 | Shlomo |
| 6,304,776 B1 | | 10/2001 | Muntermann |
| 6,322,558 B1 | | 11/2001 | Taylor |
| 6,325,799 B1 | | 12/2001 | Goble |
| 6,391,024 B1 | | 5/2002 | Sun |
| 6,423,057 B1 | | 7/2002 | He |
| 6,470,236 B2 | | 10/2002 | Ohtsuki |
| 6,569,160 B1 | * | 5/2003 | Goldin ............ A61B 18/12 600/427 |
| 6,696,844 B2 | | 2/2004 | Wong |
| 6,800,986 B2 | | 10/2004 | Yamauchi |
| 6,837,886 B2 | | 1/2005 | Collins et al. |
| 6,845,264 B1 | | 1/2005 | Skladnev et al. |
| 6,882,885 B2 | | 4/2005 | Levey, Jr. et al. |
| 7,011,410 B2 | | 3/2006 | Bolger et al. |
| 7,060,965 B2 | | 6/2006 | Vidovic et al. |
| 7,591,816 B2 | * | 9/2009 | Wang ............ A61B 18/1492 606/41 |
| 8,021,361 B2 | | 9/2011 | Paul |
| 8,567,265 B2 | * | 10/2013 | Aeby ............ A61B 5/0084 606/1 |
| 2001/0034501 A1 | | 10/2001 | Tom |
| 2002/0023749 A1 | | 2/2002 | Kirk |
| 2002/0123749 A1 | * | 9/2002 | Jain ............ A61B 18/1492 606/41 |
| 2003/0056351 A1 | | 3/2003 | Wilkie |
| 2003/0130615 A1 | | 7/2003 | Tom |
| 2003/0204184 A1 | | 10/2003 | Ferek-Patric |
| 2004/0199156 A1 | | 10/2004 | Rioux |
| 2004/0210214 A1 | | 10/2004 | Knowlton |
| 2004/0217674 A1 | | 11/2004 | Bianchini |
| 2005/0159739 A1 | | 7/2005 | Paul et al. |
| 2005/0159741 A1 | | 7/2005 | Paul et al. |
| 2005/0267467 A1 | | 12/2005 | Paul et al. |
| 2007/0078484 A1 | | 4/2007 | Talarico |
| 2007/0106291 A1 | * | 5/2007 | Thao ............ A61B 18/14 606/41 |
| 2008/0255629 A1 | | 10/2008 | Jenson |
| 2008/0275442 A1 | | 11/2008 | Saurav |
| 2009/0158852 A1 | | 6/2009 | Saurav |

FOREIGN PATENT DOCUMENTS

| | | |
|---|---|---|
| WO | 1998/017185 | 4/1998 |
| WO | 2004/098694 | 11/2004 |
| WO | 2005039835 | 5/2005 |

OTHER PUBLICATIONS

Author: , Title: General Pharmacology Samba—Blood Pressure Systems Citation: http://www.bioseb.com/bioseb/anglais/default/item id=94 cat id=3 Samba%20-%20Pressure%20System.php Reference pp. 1-4 Publication Date: Oct. 2007.

Author: , Title: Micro Pressure Measurement System—Product Overview Citation: Biopac Systems, Inc. Reference pp. 1-39 Publication Date: Aug. 2007.

Author: , Title: Need to Know Citation: Medical Product Manuf. news Publication Date: Sep. 2007.

Author: , Title: The Samba Technology Citation: Samba Sensors; www.samba.se/index2.cfm?PageID=45 Publication Date: Oct. 2007.

Supplementary European Search Report in EP Application No. 06836608.7 (dated Aug. 4, 2010).

An International Search Report for PCT Application No. PCT/US06/39881, dated Jun. 30, 2008, 3 pgs.

An International Search Report for PCT Application No. PCT/US06/42119, dated Sep. 13, 2007, 1 pg.

An International Search Report for PCT Application No. PCT/US2007/080981, dated Apr. 16, 2008, 3 pgs.

An International Search Report for PCT Application No. PCT/US07/80983, dated Apr. 2, 2008. 3 pgs.

Eick, et al. "The LETR-Principle: A Novel Method to Assess Electrode-Tissue Contact in Radiofrequency Ablation", Jul. 1998.

(56) References Cited

OTHER PUBLICATIONS

Measurement Specialties, Inc. "Piezo Film Sensors Technical Manual", Apr. 1999.

* cited by examiner

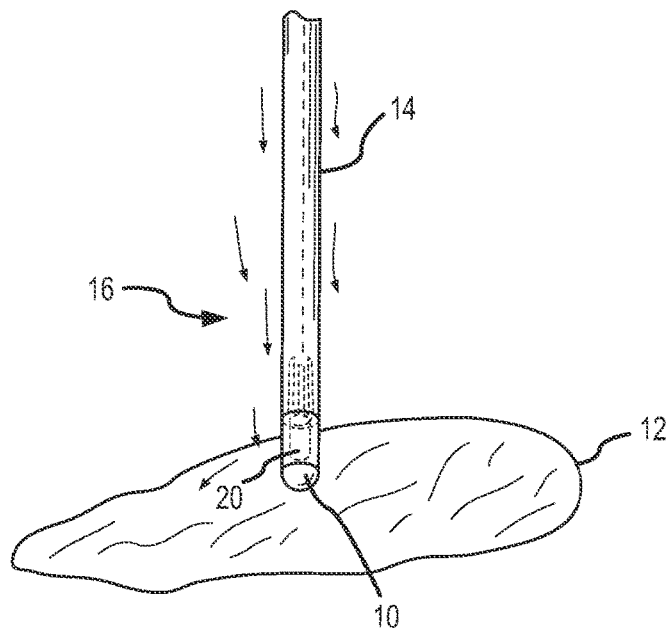
FIG.1a
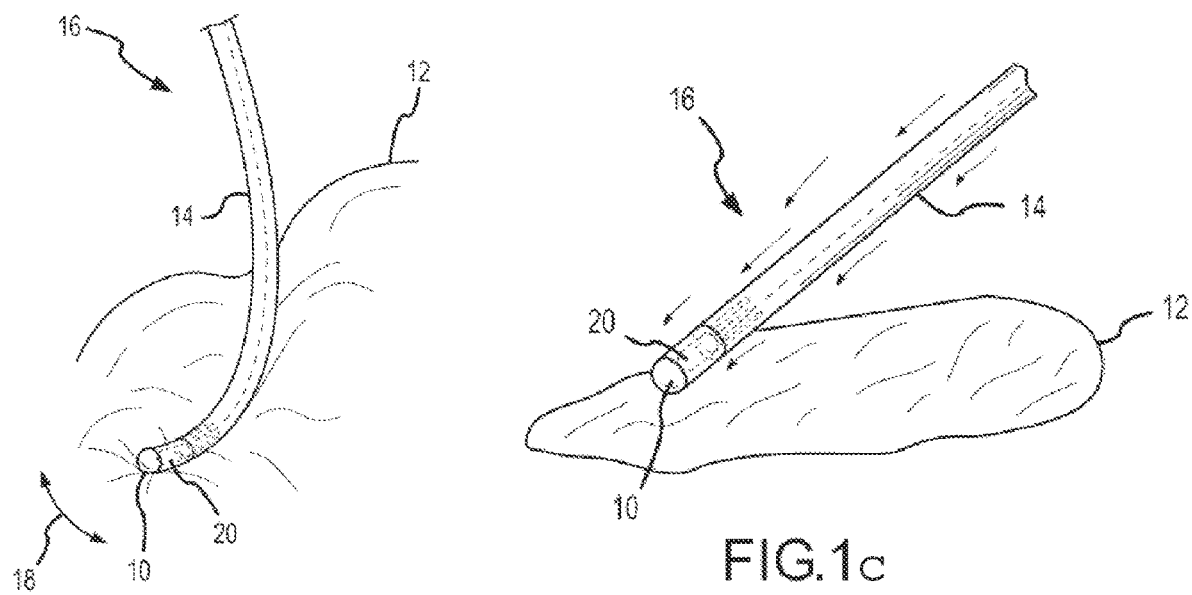
FIG.1b
FIG.1c

SYSTEMS AND METHODS FOR ASSESSING TISSUE CONTACT

CROSS-REFERENCE TO RELATED APPLICATIONS

This application is a continuation of U.S. application Ser. No. 11/617,364, filed 28 Dec. 2006, now U.S. Pat. No. 8,672,936 (the '364 application) which is a continuation-in-part of U.S. application Ser. No. 11/553,965, filed 27 Oct. 2006, now U.S. Pat. No. 8,021,361 (the '965 application), which claims the benefit of U.S. provisional application No. 60/730,634, filed 27 Oct. 2005 (the '634 application). This application is also a continuation-in-part of U.S. application Ser. No. 11/549,100, filed 12 Oct. 2006, now U.S. Pat. No. 8,679,109 (the '100 application), which claims the benefit of U.S. provisional application No. 60/727,164, filed 13 Oct. 2005 (the '164 application), all of which are hereby incorporated by reference as though fully set forth herein.

BACKGROUND OF THE INVENTION a. Field of the Invention

The instant invention is directed toward assessing tissue contact for flexible tip devices which may be implemented for use with catheters, and methods of manufacturing and using the flexible tip devices for assessing tissue contact. In particular, the flexible tip devices of the present invention may comprise one or more piezoelectric sensors for assessing tissue contact for mapping, ablation or other procedures.

b. Background Art

Various devices (e.g., electrode sensors, thermal sensors, ablation electrodes, etc.) may be implemented in catheters inserted into the patient's body (e.g., the patient's heart) for use in a wide variety of medical procedures, such as "mapping" the interior of the heart, thermal "mapping," and tissue ablation, to name only a few examples. It is often desirable to determine the level of tissue contact between the device being used and the tissue the device is being used on.

By way of illustration, sensor output is only meaningful for mapping procedures when the sensors are in sufficient contact with the tissue being mapped. "False" signals received when the sensor is not in good or sufficient contact with the tissue may result in inaccurate mapping of the tissue (e.g., the interior of a patient's heart).

By way of further illustration, it is desirable to control the level of contact to form ablative lesions. In particular, it is desirable to maintain a constant level of contact between the ablation electrode and the cardiac tissue in order to elevate tissue temperature to around 50° C. and form lesions in the cardiac tissue via coagulation necrosis. Such lesions change the electrical properties of the cardiac tissue and may lessen or eliminate undesirable atrial fibrillations when formed at specific locations in cardiac tissue. Insufficient contact during the ablation procedure may result in poor lesion formation and/or damage to surrounding tissue in the heart Tissue contact is not always readily determined using conventional fluoroscopy techniques. Instead, the physician determines tissue contact based on his/her experience maneuvering the catheter. Such experience only comes with time, and may be quickly lost if the physician does not use the catheter on a regular basis. When used inside the heart, the beating heart further complicates matters by making it difficult to assess and maintain sufficient contact with the tissue for a sufficient length of time. If contact with the tissue cannot be properly maintained, advantages of using the device may not be fully realized.

BRIEF SUMMARY OF THE INVENTION

It is desirable to be able to assess tissue contact for various procedures, including but not limited to mapping and ablation procedures within the heart. Positioning a flexible tip device (e.g., a sensing electrode, thermal sensor, ablation electrode, etc.) against a tissue creates contact stresses, which may be measured by implementing one or more piezoelectric sensors operatively associated with the flexible tip device. The piezoelectric sensor(s) generates a voltage signal corresponding to the contact stresses.

In an exemplary embodiment, one or more piezoelectric sensor is operatively associated with a flexible tip device. Output from the piezoelectric sensor(s) enables a user (e.g., a physician or technician) to position the flexible tip device against a moving tissue with the desired amount of pressure for the procedure.

An exemplary tissue contact sensing system comprises a flexible tip device. At least one piezoelectric sensor is housed within the flexible tip device. The at least one piezoelectric sensor is responsive to contact stress of the flexible tip device by generating electrical signals corresponding to the amount of contact stress. An output device is electrically connected to the at least one piezoelectric sensor. The output device receives the electrical signals for assessing tissue contact by the flexible tip device.

Another exemplary system comprises flexible tip means for practicing a medical procedure. The system also comprises means for generating piezoelectric signals corresponding to contact stress of the flexible tip means. The system also comprises means for assessing tissue contact of the flexible tip means based at least in part on the piezoelectric signals.

An exemplary method of assessing tissue contact comprises: generating piezoelectric signals in response to stress caused by a flexible tip device contacting a tissue, and outputting piezoelectric signals for assessing tissue contact. Output may be conveyed to the user in real-time (e.g., at a display device or other interface) so that the user can properly position the flexible tip device on the tissue with the desired level of contact for the procedure. For example, the user may increase contact pressure if the output indicates insufficient contact for the procedure. Or for example, the user may reduce contact pressure if the output indicates too much contact for the procedure.

An exemplary method for assembling a flexible tip device comprises: positioning a piezoelectric film into a lumen of the flexible tip device, applying a flexible polymer into the lumen of the flexible tip device to maintain a position of the piezoelectric film, and curing the flexible polymer. Optionally, the piezoelectric film may be formed into a substantially J or U (or other desired shape) before applying the flexible polymer. More flexible polymer may be applied to the piezoelectric film after curing to insulate the piezoelectric film.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1a-c illustrate exemplary contact between a flexible tip device and a tissue.

FIG. 2b is a cross-sectional view of the flexible tip device taken along lines 2b-2b in FIG. 2a.

DETAILED DESCRIPTION OF THE INVENTION

Figure 2:
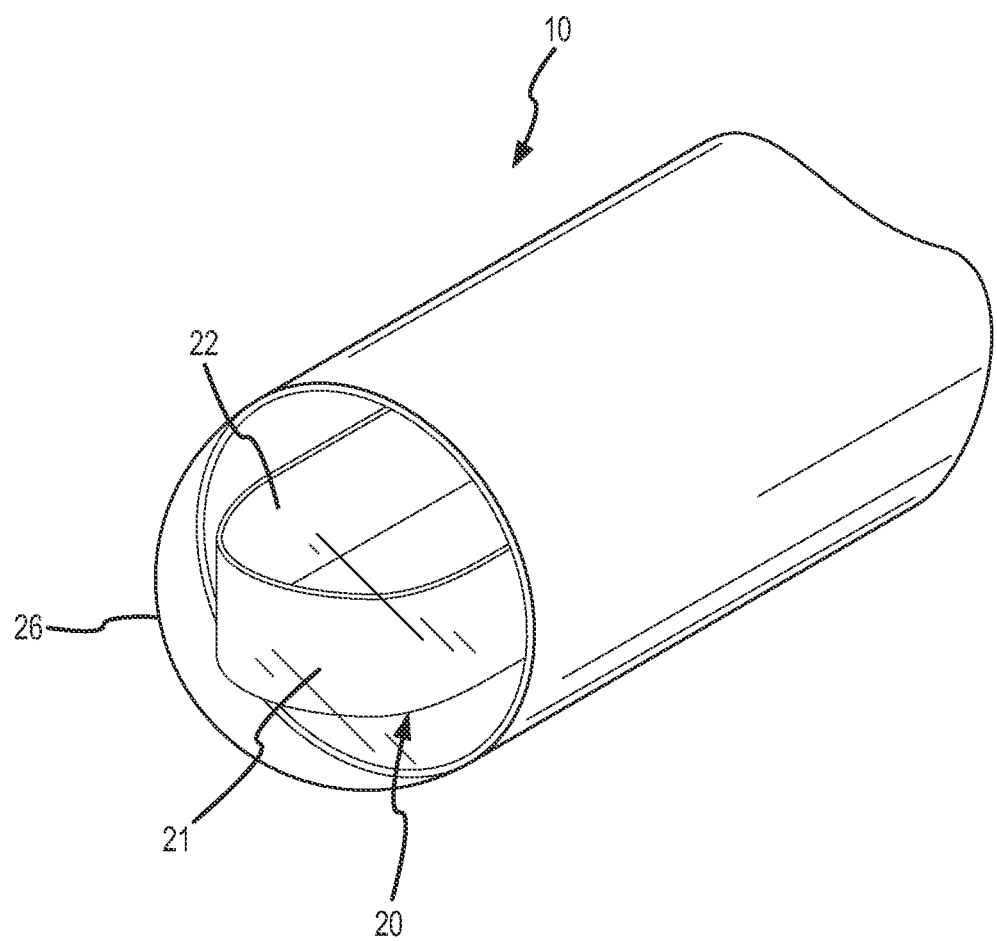
FIG. 2 is a perspective view of an exemplary flexible tip device operatively associated with a piezoelectric sensor for assessing tissue contact.

Exemplary embodiments of systems and methods to assess contact between a flexible tip device and a tissue are depicted in the figures. Exemplary systems comprise a flexible tip device (e.g., sensing electrode, thermal sensor, or ablation electrode) which may be inserted into the patient using a catheter. During an exemplary procedure, a user (e.g., the patient's physician or a technician) may insert the catheter into one of the patient's blood vessels, e.g., through the leg or the patient's neck. The user, guided by a real-time fluoroscopy imaging device, moves the catheter to the desired position within the patient's body (e.g., into the patient's heart).

When the catheter reaches the patient's heart, the flexible tip device may be used to perform various procedures, such as, electrically or thermally mapping the myocardium (i.e., muscular tissue in the heart wall), or tissue ablation procedures. Determining contact with the tissue is often critical. In ablation procedures, for example, the amount of contact is critical to form sufficiently deep ablative lesions on the tissue without damaging surrounding tissue in the heart.

As described further below, the system may include one or more piezoelectric sensors which generate electric signals in response to stresses caused by contact with a surface (e.g., tissue within the beating heart). Accordingly, embodiments of the present invention provide a number of advantages, including, for example, facilitating enhanced tissue contact in difficult environments such as a moving surface inside a beating heart.

FIG. 1a-c illustrate exemplary contact between a flexible tip device 10 (e.g., an electrode sensor, thermal sensor, or ablative electrode) and a tissue 12 (e.g., myocardium). The flexible tip device 10 may be inserted through a shaft 14 of catheter 16. The catheter shaft 14 may be made of a plastic or other suitable material which facilitates insertion into the patient's body (e.g., the patient's heart) through the blood vessels.

Optionally, the flexible tip device 10 may be electrically connected via suitable wiring through the catheter shaft 14 to a generator (not shown), such as, e.g., a radio frequency (RF) generator. For example, where the flexible tip device 10 is an electrode, the RF generator is operable to emit electrical energy (e.g., RF radiation) near the distal end of the electrode for mapping operations or forming ablation lesions on the tissue 12.

During use, a user may operate a handle portion (not shown) of the catheter 16 to manually position the catheter 16 inside the patient's body, e.g., so that the flexible tip device 10 is in contact with the tissue 12. In FIGS. 1a and 1c, the flexible tip device 10 is shown having little, if any, contact with the tissue 12, e.g., the flexible tip device 10 may be "floating" adjacent the tissue 12. In FIG. 1b, the flexible tip device 10 is shown in contact with the tissue 12.

When the flexible tip device 10 is in sufficient or "good" contact with the tissue 12, the flexible tip device 10 may move or be deflected by movement of the tissue 12 generally in the directions illustrated by arrows 18. Movement of the flexible tip device 10 may be measured in real-time using at least one piezoelectric sensor 20 to assess contact with the tissue 12, as described more fully below.

Before continuing, it is noted that the contact and motion illustrated in FIG. 1b is shown for purposes of illustration and is not intended to be limiting. Other contact and motion may also exist and/or be desired by the user. The definition of sufficient or "good" contact may depend at least to some extent on the procedure being performed and/or various operating conditions, such as, e.g., the type of tissue, desired depth of the ablation lesion, and power and duration of the applied RF energy, to name only a few examples.

It is also noted that other components typical of systems which are conventionally implemented for various procedures, are not shown or described herein for purposes of brevity. Such components may nevertheless also be provided as part of, or for use with, the flexible tip device 10. For example, these systems commonly include or are used in conjunction with an ECG recording system, and/or various controls for performing the procedure. Such components are well understood in the medical devices arts and therefore further explanation is not necessary for a complete understanding of the invention.

Figure 2A:
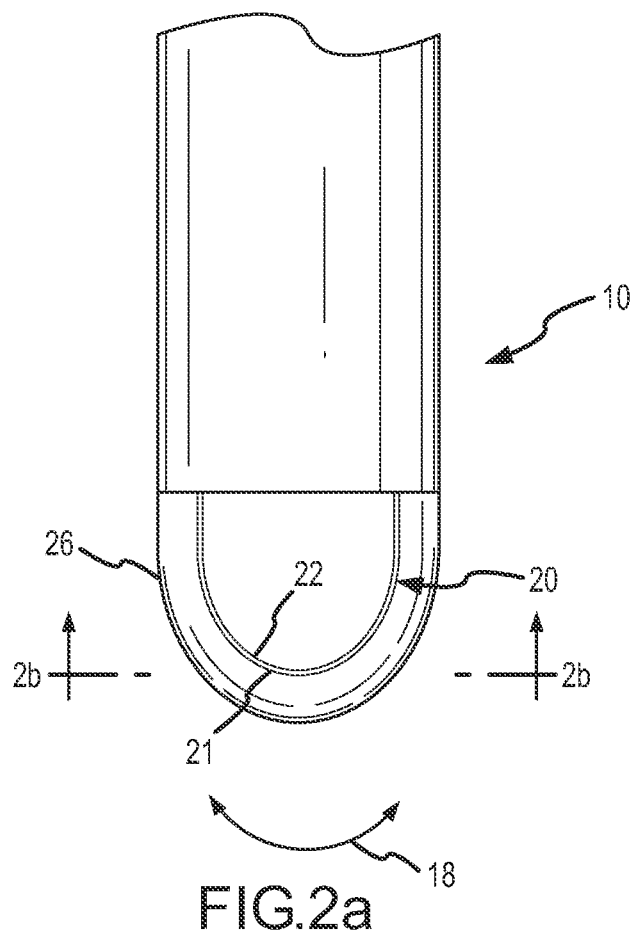
FIG. 2a is a side view of the flexible tip device shown in FIG. 2.
Figure 2B:
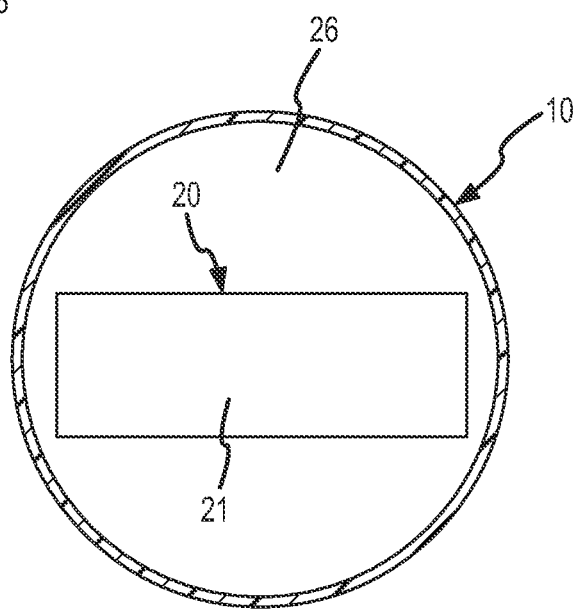

As previously mentioned, one or more piezoelectric sensors 20 may be operatively associated with the flexible tip device 10 to measure stress when the flexible tip device 10 is in contact with the tissue 12. FIG. 2 is a perspective view of a distal tip portion (e.g., the portion shown in contact with the tissue 12 in FIG. 1b) of an exemplary flexible tip device 10 operatively associated with a piezoelectric sensor 20 for assessing tissue contact. FIG. 2a is a side view of the flexible tip device 10 shown in FIG. 2. FIG. 2b is a cross-sectional view of the flexible tip device 10 taken along lines 2b-2b in FIG. 2a. In this embodiment, the piezoelectric sensor 20 is substantially U-shaped, although other shapes are also contemplated as being within the scope of the invention.

In an exemplary embodiment, the piezoelectric sensor 20 may include a piezoelectric film 21 laminated on a support structure 22 anchored within the flexible tip device 10. Optionally, piezoelectric film may be laminated to opposite sides of the support structure 22. Signals from the piezoelectric films on opposite sides of the support structure 22 may be combined to improve the sensitivity of the contact sensing. Additionally, because the stress response of piezoelectric materials is anisotropic, the two sides may be oriented differently with respect to each other to either attenuate directional differences in sensitivity or provide directional information of the tissue contact.

Other means for supporting the piezoelectric sensor 20 within the flexible tip device 10 are also contemplated. For example, the piezoelectric sensor 20 may be provided without the support structure 22 and integrally molded within the flexible tip device 10. These and other methods for providing the piezoelectric sensor 20 in the flexible tip device 10 will be readily apparent to those having ordinary skill in the art after becoming familiar with the teachings herein.

The piezoelectric sensor 20 may be provided within a flexible polymer or compliant section 26 of the flexible tip device 10. In addition to housing the piezoelectric sensor 20 in the flexible tip device 10, and protecting the piezoelectric sensor 20 from external damage or corrosion, the compliant section 26 may serve as a low pass mechanical filter. That is, the compliant section 26 attenuates high frequency "noise" signals caused, e.g., by minor vibrations from intermittent contact during positioning of the flexible tip device 10 adjacent the tissue 12. Accordingly, high frequency noise signals are damped, or even non-existent, as output for the user. However, the piezoelectric sensor 20 does not need to be provided in a compliant section. For example, the piezoelectric sensor 20 may instead be provided within an airspace formed in the flexible tip device 10.

Electrical wiring (not shown) may be connected to the piezoelectric sensor 20 and a ground. The electrical wiring may extend through the lumen of the flexible tip device 10 to deliver electrical signals from the piezoelectric sensor 20 to a data acquisition/processing/output device (also not shown), such as, e.g., an echocardiogram (ECG) device. Alternatively, a wireless connection may be implemented, e.g., by providing a transmitter in the catheter and a receiver in association with the data acquisition/processing/output device.

In an exemplary embodiment, the flexible tip device 10 may be assembled as follows. A strip of piezoelectric film 21 is laminated to the support structure 22 and then formed (e.g., bent) into the desired shape (e.g., the substantially U-shape shown in FIG. 2). The formed piezoelectric sensor 20 may then be positioned in the lumen of the flexible tip device 10. While the laminated piezoelectric film is in the desired position within the lumen of the flexible tip device 10, a flexible polymer (e.g., flexible ultraviolet (UV) adhesive) may be applied into the lumen of the flexible tip device 10 to hold the ends of the piezoelectric sensor 20 in place so that it does not move and maintains the desired shape (e.g., the substantially U-shape). The adhesive may then be cured (e.g., using UV light). More adhesive may then be applied around the remainder of the piezoelectric sensor 20 so that it covers or insulates the piezoelectric sensor 20. The additional adhesive may then be cured to form compliant section 26.

It is noted that the configuration with the piezoelectric sensor 20 housed within the flexible tip device 10 enable manufacturing of relatively small sizes and therefore are particularly suitable for use, e.g., in so-called brush electrodes. However, these embodiments are not limited to any particular size or use. It is also noted that other shapes and arrangements of the piezoelectric sensor(s) 20 are also contemplated, as will be readily apparent to those having ordinary skill in the art after becoming familiar with the teachings herein.

In use, the piezoelectric sensor 20 responds to electrode-tissue contact stresses by generating electrical energy (e.g., a voltage). Accordingly, when the flexible tip device 10 is positioned in contact with the tissue 12, piezoelectric sensor 20 generates an electrical signal corresponding to stress caused by this contact. The resulting electrical signal may be processed and/or otherwise output for the user so that the user is able to determine when the flexible tip device 10 contacts the tissue 12.

Piezoelectric sensors which generate electrical energy in response to applied mechanical stress are well-understood in the electro-mechanical arts. In general, piezoelectric sensors comprise a piezoelectric material which contains positive and negative electrical charges. In a neutral or "non-stressed" state, these electrical charges are symmetrically distributed in the piezoelectric material such that the material exhibits an overall neutral electrical charge. However, subjecting the piezoelectric material to a mechanical stress (e.g., flexure, pressure, and/or tension) disturbs the symmetrical distribution of electrical charges, thereby generating electrical energy across the material. Even minor deformation of some piezoelectric materials (e.g., on the order of nanometers) may generate a measurable voltage signal. Operation of piezoelectric material may be better understood with brief reference to FIG. 3*a-c*

Figure 3A:
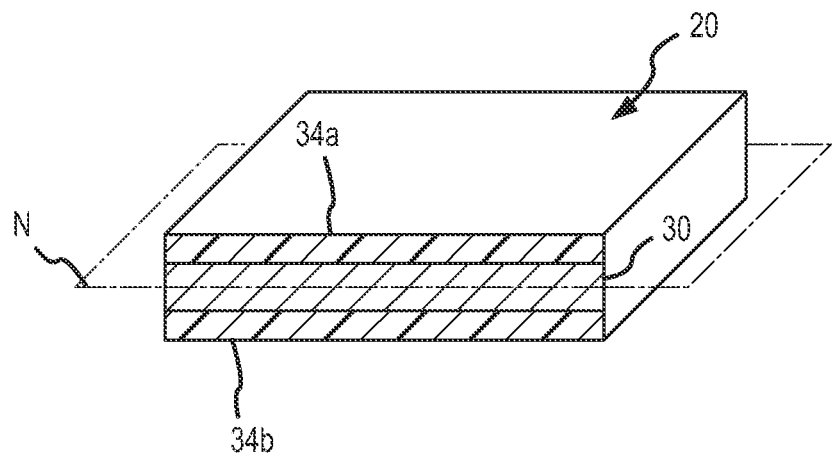
FIG. 3a is a sectional view of an exemplary piezoelectric sensor which may be implemented in the flexible tip device.
Figure 3B:
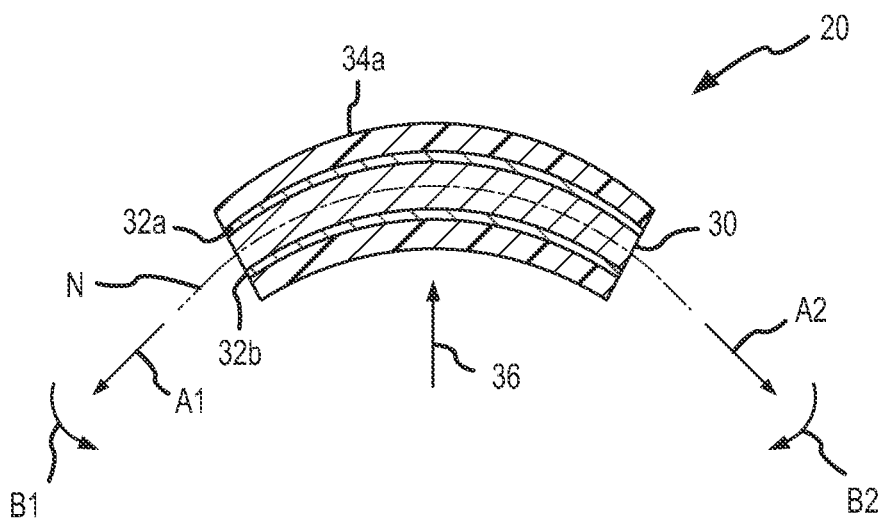
In FIG. 3b-c, the piezoelectric sensor is shown in exaggerated form as it may respond to various stresses.
Figure 3C:
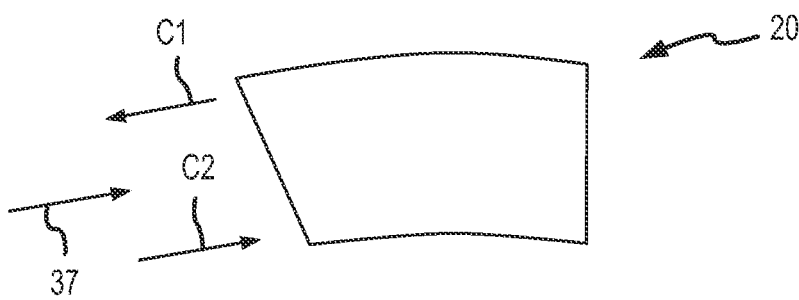

FIG. 3*a* is a cross-sectional perspective view of a portion of an exemplary piezoelectric sensor 20 which may be implemented in the flexible tip device. In FIG. 3*b-c*, the piezoelectric sensor 20 is shown in exaggerated form as it may respond to various stresses, wherein FIG. 3*b* is a side-view of the piezoelectric sensor 20 shown in FIG. 3*a*, and FIG. 3*c* is a top-view of the piezoelectric sensor 20 shown in FIG. 3*a*.

In an exemplary embodiment, the piezoelectric sensor 20 may be a laminated sensor or film having a plurality of laminated layers. Although not required, laminating the sensor increases its sensitivity. Piezoelectric films are flexible, lightweight, and tough engineered plastic that is available in a wide variety of thicknesses and large areas. Among other advantages, piezoelectric film has a low acoustic impedance which is close to that of water, human tissue, and other organic materials. For example, the acoustic impedance of piezoelectric film is only about 2.6 times the acoustic impedance of water. Piezoelectric film also has a low density and excellent sensitivity, and is mechanically tough. When extruded into a thin film, piezoelectric polymers can be directly attached to a support structure without distributing its mechanical range of motion. Piezoelectric film is therefore well suited to strain-sensing applications requiring very wide bandwidth and high sensitivity.

In FIG. 3*a*, the laminated layers of piezoelectric sensor 20 may comprise a piezoelectric material 30 "sandwiched" between metal layers 32*a* and 32*b* and protective coating 34*a* and 34*b*. Metal layers 32*a* and 32*b* may be any suitable metal, e.g., a thin layer of silver ink. The metal layers 32*a* and 32*b* serve to collect electrical charge generated by the piezoelectric material 30, e.g., for delivery as electrical signals via electrical wiring to a data acquisition/processing/output device. Metal layers 32*a* and 32*b* serve to collect electrical energy in response to stress of the piezoelectric material 30. Piezoelectric material, such as PVDF (Kynar), is commercially available as a highly-sensitive, thin, flexible polymer film, which makes it particularly desirable for use with deflectable catheters. Protective coating 34*a* and 34*b* may be any suitable material, e.g., Mylar®.

It is noted that the laminated layers of piezoelectric sensor 20 are not limited to any particular material and/or configuration. For example, the piezoelectric sensor 20 is not limited to use with separate metal layers 32*a* and 32*b*. Nor is the piezoelectric sensor 20 limited to the generally rectangular configuration shown in FIG. 3*a*.

In an exemplary embodiment, the piezoelectric material 30 may comprise a thin, flexible, polymer-based material. One such piezoelectric film is a polyvinylidene fluoride (PVDF) film commercially available from the Sensor Products Division of Measurement Specialties, Inc. (Norristown, Pa.). This PVDF film is approximately 28 µm thick, enabling the PVDF film to be readily housed within the catheter shaft 14.

In addition, this PVDF film has a wide frequency range of about 0.001 Hz to $10^9$ Hz and a high dynamic stress constant ($g_{31}$=216×$10^{-3}$ Vm/N). For purposes of illustration, other common piezoelectric materials, such as lead zirconate titanate (PZT) has a dynamic stress constant ($g_{31}$) of 10×$10^{-3}$ Vm/N, and barium titanium oxide ($BaTiO_3$) has a dynamic stress constant ($g_{31}$) of 5×$10^{-3}$ Vm/N. Accordingly, the PVDF film is very sensitive, exhibiting a relatively high voltage response to relatively small mechanical stresses, and is therefore well-suited for measuring dynamic stresses and strains.

Of course the piezoelectric sensor 20 described above with reference to FIG. 3a is for purposes of illustration and not intended to be limiting. Other piezoelectric sensors may also be implemented, and are not limited to laminated piezoelectric film. Nor are piezoelectric sensors limited to use with any particular type or size of piezoelectric material. Selection of piezoelectric sensor 20 for use with the flexible tip device 10 may be application-specific and depend at least in part on one or more design considerations, such as, but not limited to, the desired sensitivity and/or spatial constraints for housing the piezoelectric sensor.

Piezoelectric sensor 20 is shown in FIG. 3a in a neutral state. In the neutral state, the piezoelectric material 30 is not subject to any stresses or strains. Accordingly, the electrical charges are symmetrically distributed on either side of the neutral plane N in the piezoelectric material 30 such that the material exhibits an overall neutral electrical charge.

The most widely used coefficients, d3n (for charge) and g3n (for voltage), possess two subscripts. The first refers to the electrical axis, while the second subscript refers to the mechanical axis. Because piezoelectric film is thin, the electrodes are only applied to the top and bottom film surfaces. Accordingly, the electrical axis is always referred to as "3", as the charge or voltage is always transferred through the thickness (n=3) of the film. The mechanical axis can be either 1, 2, or 3, because the stress can be applied to any of these axes. Typically, piezoelectric film is used in the mechanical 1 direction for low frequency sensing and actuation (<100 KHz) and in the mechanical 3 direction for high ultrasound sensing and actuation (>100 KHz). These stresses can be better understood with reference to FIGS. 3b and 3c.

FIG. 3b is a side-view of the piezoelectric sensor 20 shown in FIG. 3a. In FIG. 3b, the piezoelectric sensor 20 is shown in exaggerated form as it may respond to transverse stresses applied generally in the direction of arrow 36. In this stressed state, the piezoelectric material 30 undergoes transverse strain relative to its neutral state, as illustrated by arrows A1 and A2. The piezoelectric sensor 20 may also respond to bending stresses. In this stressed state, the piezoelectric material 30 undergoes flexural strain relative to its neutral state, as illustrated by arrows B1 and B2.

FIG. 3c is a top-view of the piezoelectric sensor 20 shown in FIG. 3a. In FIG. 3c, the piezoelectric sensor 20 is shown in exaggerated form as it may respond to longitudinal stresses applied generally in the direction of arrows 37a and 37b. In this stressed state, the piezoelectric material 30 is longitudinally strained relative to its neutral state, as illustrated by arrows C1 and C2.

In each case, these stresses disturb the symmetrical distribution of electrical charges, and electrical energy is generated across the piezoelectric material 30. In operation, this electrical energy may be collected by metal layers 32a, 32b, e.g., for delivery as an electrical signal via electrical wiring through the catheter shaft 14 to a data acquisition/processing/output device (not shown).

Returning to the piezoelectric sensor 20 shown mounted to the flexible tip device 10 in FIG. 2, it can be readily seen that piezoelectric sensor 20 is stressed or strained due to stress in the directions illustrated by arrows 18. The piezoelectric sensor 20 responds by generating electrical (voltage) signals. These electrical signals may be viewed by the user, e.g., as output on an electrical monitoring device.

Figure 4:
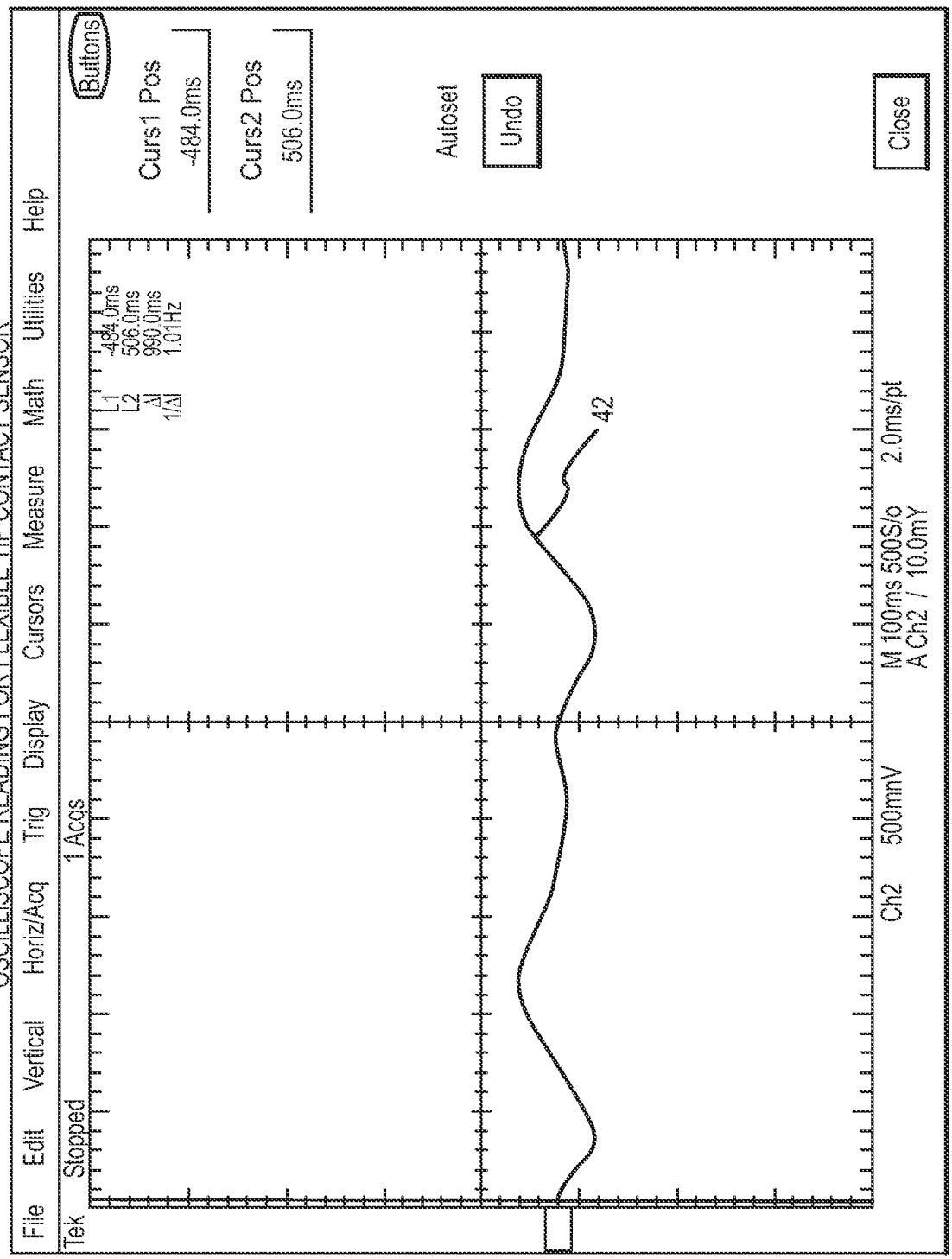
FIG. 4 shows exemplary output of an oscilloscope showing a waveform corresponding to electrical signals generated by a piezoelectric sensor for assessing tissue contact.

FIG. 4 is exemplary output of an oscilloscope showing waveform 42 corresponding to electrical signals generated by a piezoelectric sensor 20 when the flexible tip device 10 is in contact with a moving tissue 12, such as the myocardium (e.g., as shown in FIG. 1b). During operation, output such as waveform 42 may be displayed for a user, e.g., as a waveform on an ECG device.

In an exemplary embodiment, the signal strength (e.g., amplitude) from the piezoelectric sensor 20 is proportional to the amount of stress due to the contact of the flexible tip device 10 with tissue 12 (e.g., the myocardium), and therefore can be used to determine if the flexible tip device 10 is in good contact with the tissue 12. If the contact is insufficient for the procedure, then there are no peaks in the resulting waveform 42 (or the peaks are intermittent). On the other hand, a strong correlation between the heartbeat and output by the piezoelectric sensor indicates sufficient or good contact with the moving tissue.

Signal periodicity is also a strong indicator of dynamic contact assessment. For example, if the period between heartbeats corresponds well with the period output by the piezoelectric sensor 20, stresses on the piezoelectric sensor 20 are being caused by the heartbeat (and not some other reason). Accordingly, the user may use this feedback to move the flexible tip device 10 to achieve the desired tissue contact.

Before continuing, it is noted that any suitable analog and/or digital device may be implemented for indicating tissue contact to a user. In another exemplary embodiment, the electrical signals generated by piezoelectric sensor 20 may be further characterized using a suitable processing device such as, but not limited to, a desktop or laptop computer. Such processing device may be implemented to receive the voltage signal generated by the piezoelectric sensor 20 and convert it to a corresponding contact condition and output for the user, e.g., at a display device.

It is also noted that the output device is not limited to a display device. For example, the tissue contact may be output to the user as an audio signal or tactile feedback (e.g., vibrations) on the handle of the catheter 16. In any event, circuitry for conveying output of the piezoelectric sensor to a user in one form or another may be readily provided by those having ordinary skill in the electronics arts after becoming familiar with the teachings herein.

Although the flexible tip device 10 shown in FIG. 2 can bend in any angle and the piezoelectric sensor 20 still generates a signal, the piezoelectric sensor 20 is not as sensitive in directions other than those illustrated by arrows 18. That is, the piezoelectric sensor 20 is most sensitive if it is positioned or moved in a uni-planar direction from the position where the flat surface of the piezoelectric sensor 20 is facing.

To receive a signal from other directions of movement, a twisted (e.g., quarter-twisted) piezoelectric sensor may be implemented within the flexible tip device. Alternatively, multiple piezoelectric sensors 20 (or strips of piezoelectric film) may be provided within the flexible tip device 10 to receive signals in bi-planar and full-arc multi-planar orientations, as discussed in the following embodiments.

FIGS. 5 and 5a through FIGS. 10 and 10a show alternative embodiments for implementing at least one piezoelectric sensor with a flexible tip device for assessing tissue-contact. It is noted that 100-series through 600-series reference numbers are used in the embodiments shown in FIGS. 5 and 5a through FIGS. 10 and 10a, respectively, to refer to like elements described above with reference to FIGS. 2 and 2a-b. Therefore the description of some elements may not be repeated in the following discussion.

Figure 5:
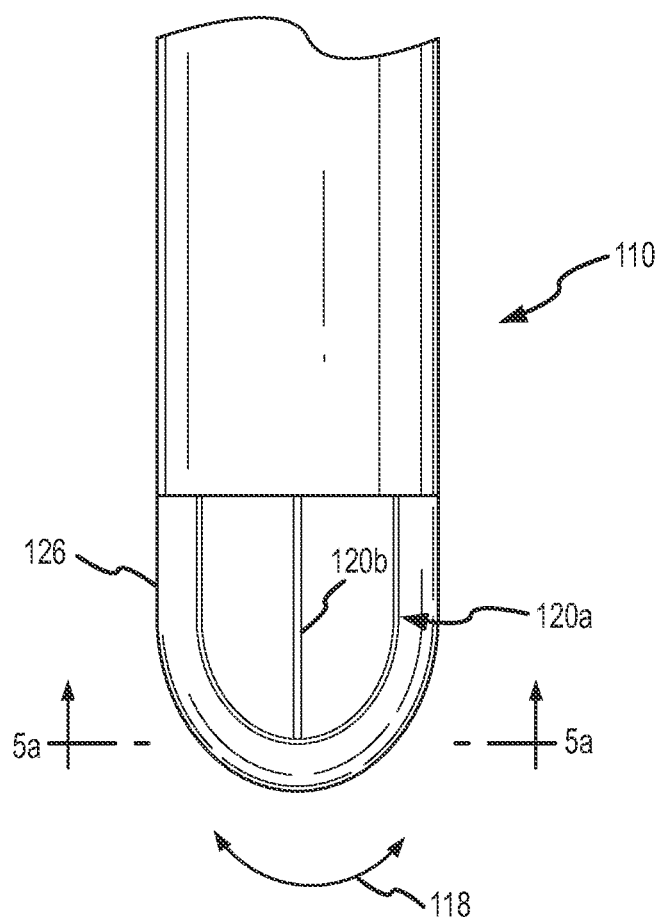
FIGS. 5 and 5a through FIGS. 10 and 10a show alternative embodiments for implementing at least one piezoelectric sensor with a flexible tip device for assessing tissue contact.
Figure 5A:
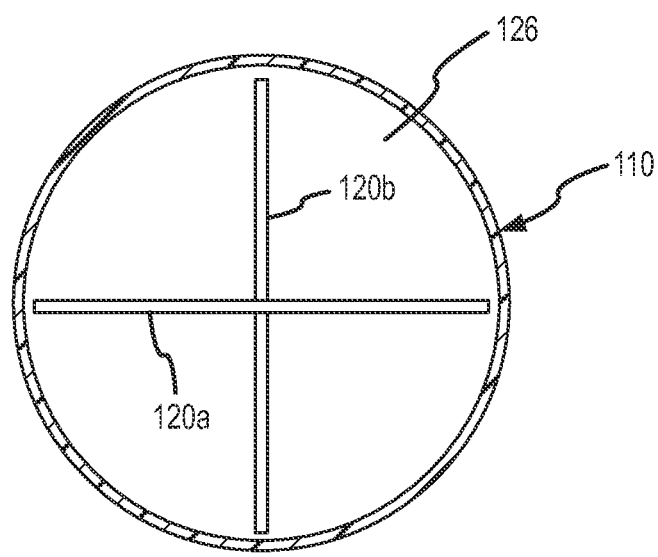

FIG. 5 is a side view of a flexible tip device 110 showing two piezoelectric sensors 120a-b. FIG. 5a is a cross-sectional view of the flexible tip device 110 taken along lines 5a-5a in FIG. 5. In this embodiment, the piezoelectric sensors 120a-b are mounted substantially perpendicular to one another.

In use, the piezoelectric sensors 120a-b respond to mechanical stresses by generating electrical energy (e.g., a voltage) which may be output to a user (e.g., as illustrated in FIG. 4). In addition to detecting tissue contact, the relative magnitude and direction of the signal obtained from each of the separate piezoelectric sensors 120a-b may be used to determine the direction and plane of contact of the flexible tip device 110. The resulting electrical signal may be processed and/or otherwise output for the user so that the user is able to determine the desired level of contact with the tissue 12.

Figure 6:
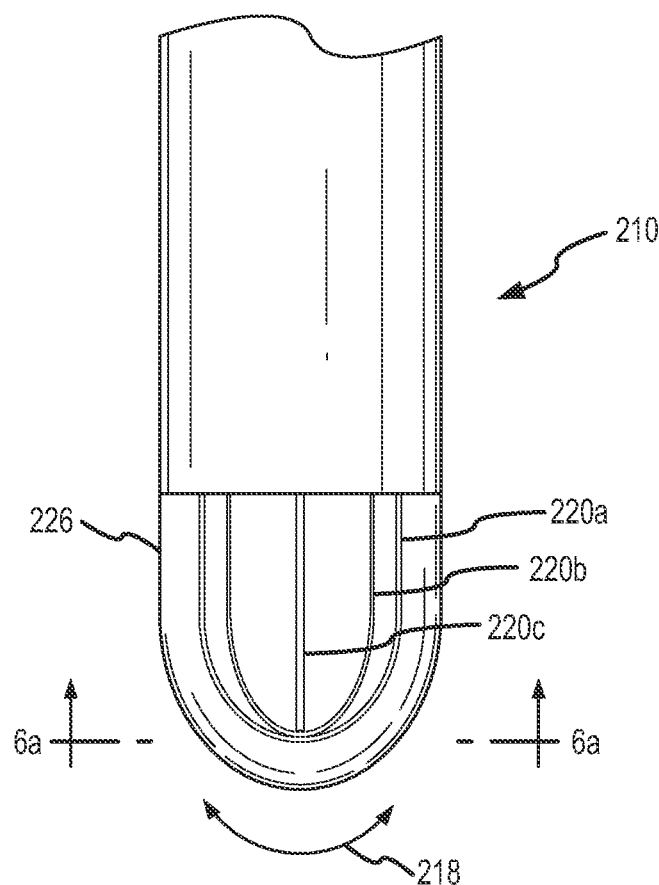
Figure 6A:
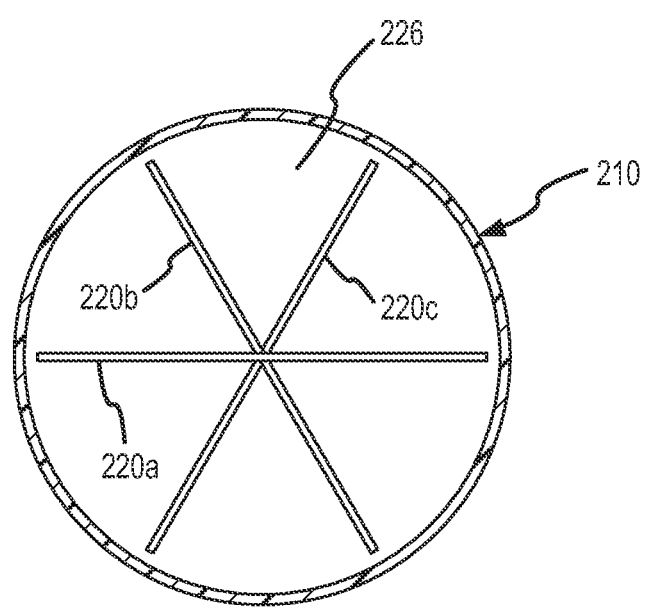

FIG. 6 is a side view of a flexible tip device 210 showing three piezoelectric sensors 220a-c. FIG. 6a is a cross-sectional view of the flexible tip device 210 taken along lines 6a-6a in FIG. 6. In this embodiment, the piezoelectric sensors 220a-c are mounted at about 30° relative to one another.

In use, the piezoelectric sensors 220a-c respond to mechanical stresses by generating electrical energy (e.g., a voltage) which may be output to a user (e.g., as illustrated in FIG. 4). In addition to detecting tissue contact, the relative magnitude and direction of the signal obtained from each of the separate piezoelectric sensors 220a-c may be used to determine the direction and plane of contact of the flexible tip device 210. The resulting electrical signal may be processed and/or otherwise output for the user so that the user is able to determine the desired level of contact with the tissue 12.

Figure 7:
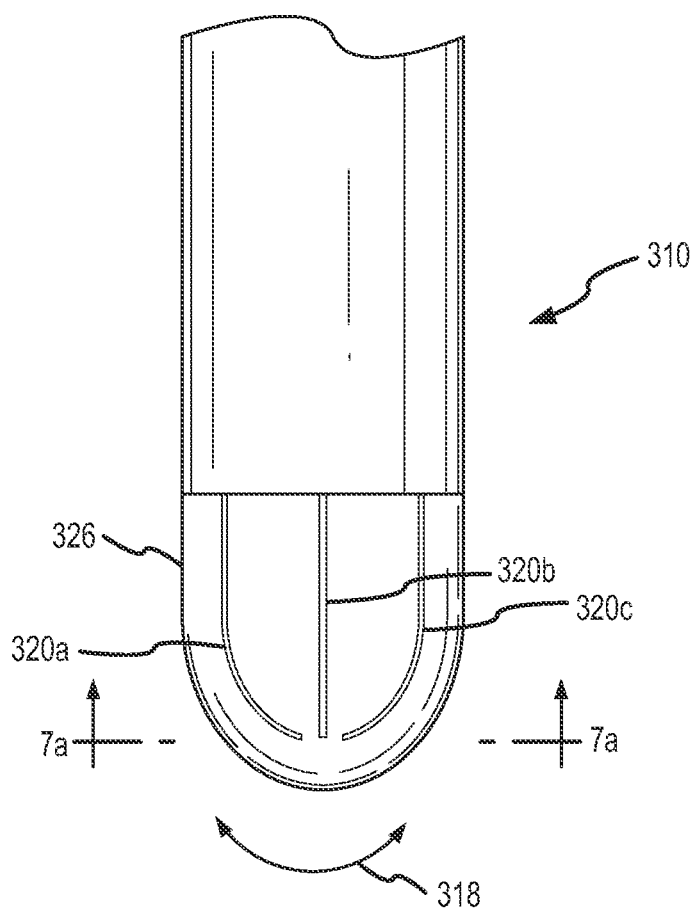
Figure 7A:
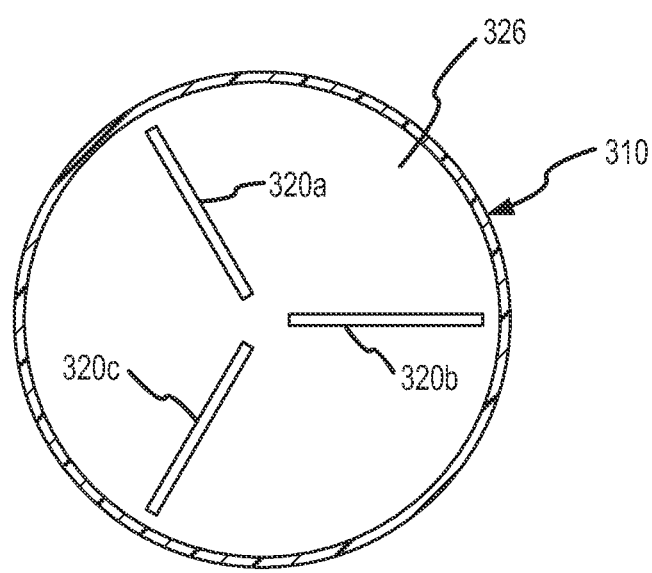

FIG. 7 is a side view of a flexible tip device 310 showing three separate piezoelectric sensors 320a-c. FIG. 7a is a cross-sectional view of the flexible tip device 310 taken along lines 7a-7a in FIG. 7. In this embodiment, the separate piezoelectric sensors 320a-c are substantially hook or J-shaped and mounted at about 120° relative to one another. This embodiment enables both axial and angular (or radial) stresses to be detected during operation. In addition, the opening formed through the center of the piezoelectric sensors 320a-c may be used with irrigated electrodes.

In use, the piezoelectric sensors 320a-c respond to mechanical stresses by generating electrical energy (e.g., a voltage) which may be output to a user (e.g., as illustrated in FIG. 4). In addition to detecting tissue contact, the relative magnitude and direction of the signal obtained from each of the separate piezoelectric sensors 320a-c may be used to determine the direction and plane of contact of the flexible tip device 310. The resulting electrical signal may be processed and/or otherwise output for the user so that the user is able to determine the desired level of contact with the tissue 12.

Figure 8:
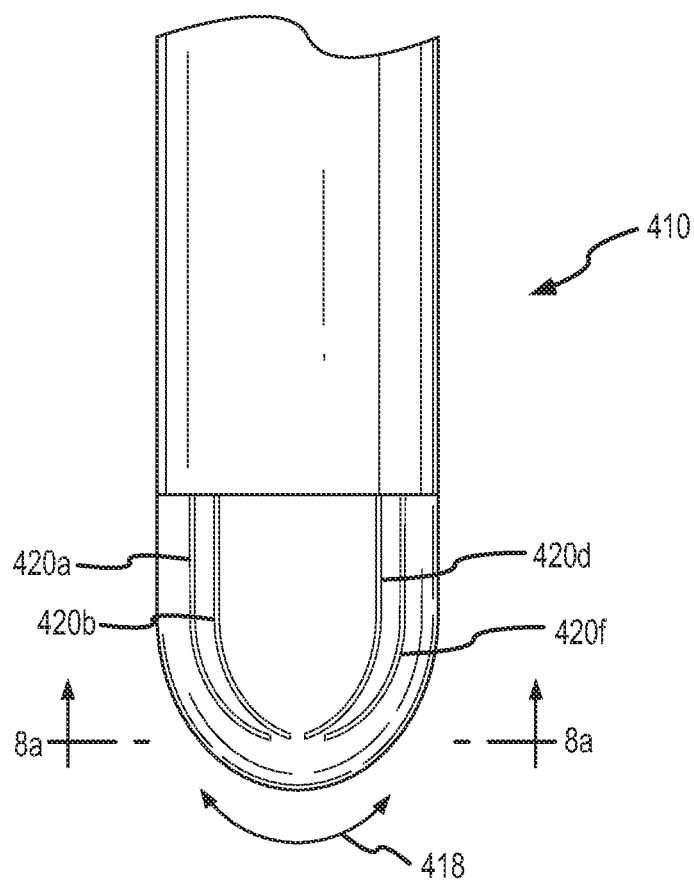
Figure 8A:
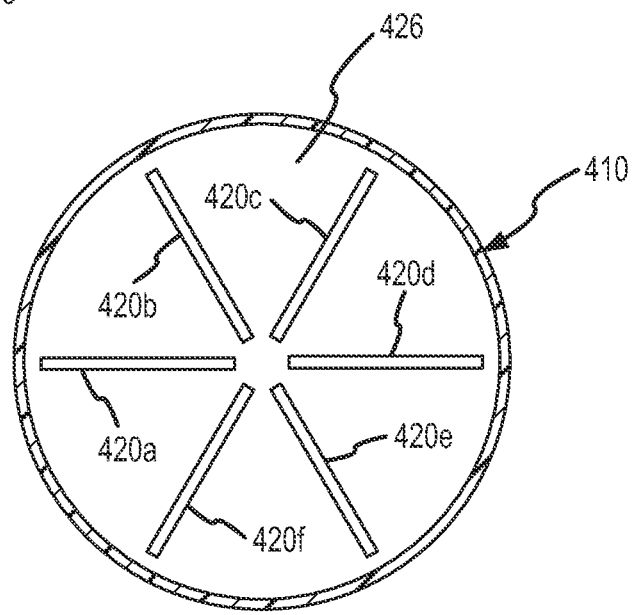

FIG. 8 is a side view of a flexible tip device 410 showing six separate piezoelectric sensors 420a-f. FIG. 8a is a cross-sectional view of the flexible tip device 410 taken along lines 8a-8a in FIG. 8. In this embodiment, the separate piezoelectric sensors 420a-f are substantially hook or J-shaped and mounted at about 30° relative to one another.

In use, the piezoelectric sensors 420a-f respond to mechanical stresses by generating electrical energy (e.g., a voltage) which may be output to a user (e.g., as illustrated in FIG. 4). In addition to detecting tissue contact, the relative magnitude and direction of the signal obtained from each of the separate piezoelectric sensors 420a-f may be used to determine the direction and plane of contact of the flexible tip device 410. The resulting electrical signal may be processed and/or otherwise output for the user so that the user is able to determine the desired level of contact with the tissue 12.

In each of the embodiments shown in FIGS. 5 and 5a through FIGS. 8 and 8a, the compliant section is non-conductive. Accordingly, if the flexible tip device is implemented as an electrode, a separate electrode material may be provided through the shaft and into the distal portion of the flexible tip device. Alternatively, the distal portion of the flexible tip device may include a conductive material integrally formed as part of the flexible tip device to deliver RF energy during the procedure (e.g., for mapping or ablation), as explained in more detail below with reference to the embodiments shown in FIGS. 9 and 9a through FIGS. 10 and 10a.

Figure 9:
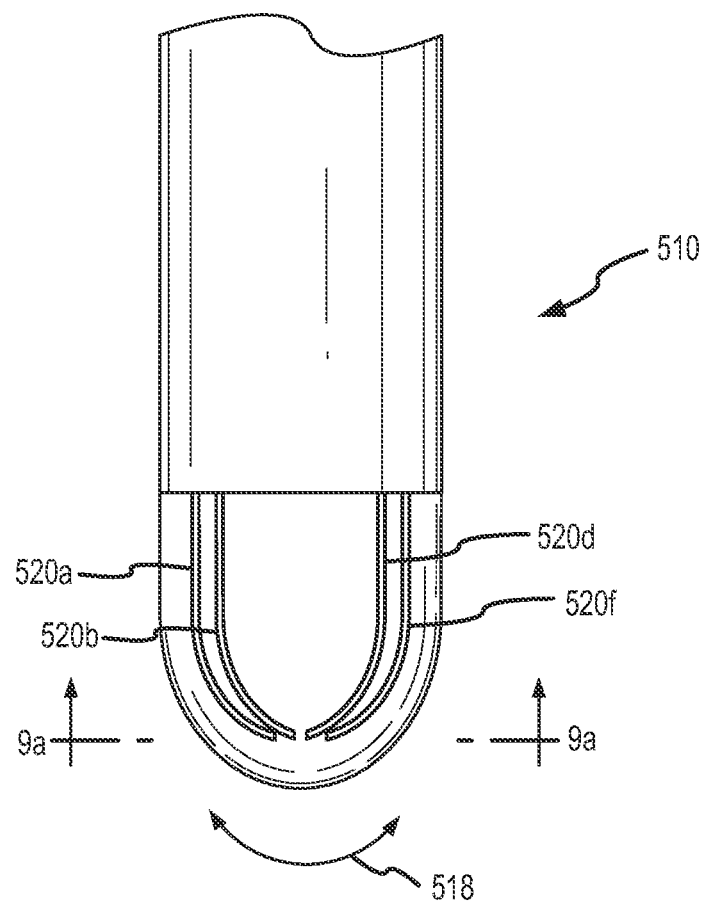
Figure 9A:
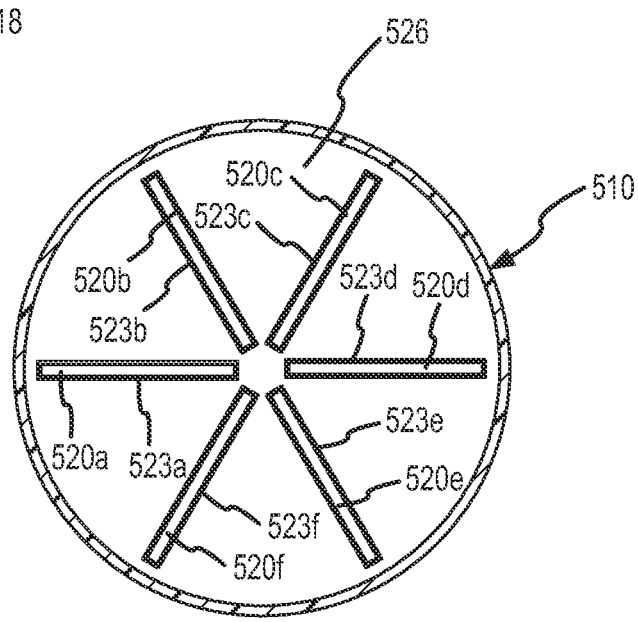

FIG. 9 is a side view of a flexible tip device 510 showing six separate piezoelectric sensors 520a-f. FIG. 9a is a cross-sectional view of the flexible tip device 510 taken along lines 9a-9a in FIG. 9. In this embodiment, the separate piezoelectric sensors 520a-f are substantially hook or J-shaped and mounted at about 30° relative to one another. In addition, each of the piezoelectric sensors 520a-f are individually insulated (insulation 523a-f) and provided in a conductive compliant section 526. In use, the conductive compliant section 526 may be use to deliver RF energy during the procedure (e.g., for mapping or ablation).

Figure 10:
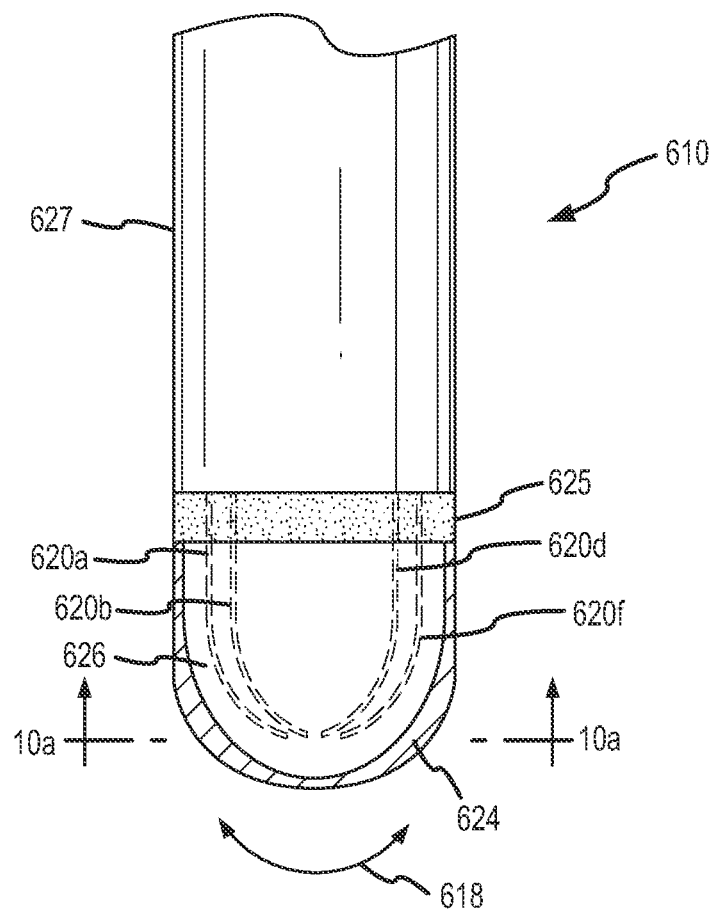
Figure 10A:
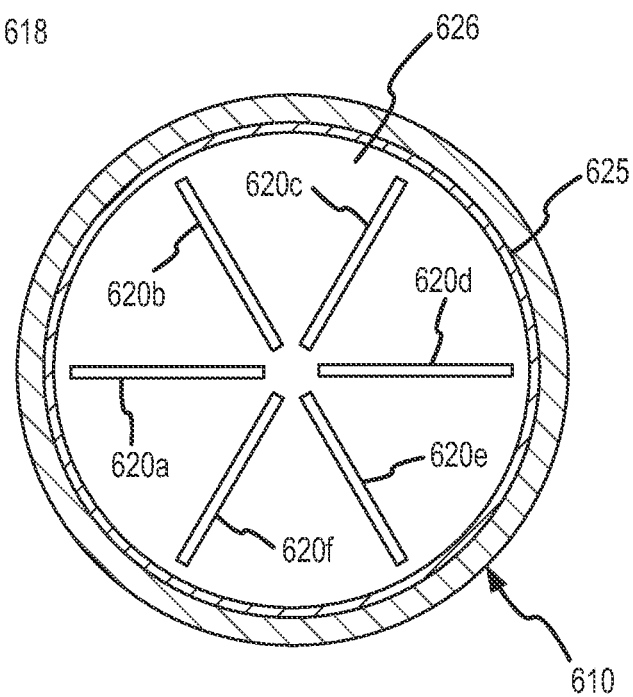

FIG. 10 is a side view of a flexible tip device 610 showing six separate piezoelectric sensors 620a-f. FIG. 10a is a cross-sectional view of the flexible tip device 610 taken along lines 10a-10a in FIG. 10. In this embodiment, the separate piezoelectric sensors 620a-f are substantially hook or J-shaped and mounted at about 30° relative to one another and provided in a non-conductive compliant section 626. In addition, a conductive layer 624 may be provided surrounding the non-conductive compliant section 626. A non-conductive shield 625 is provided between the shaft 627 of the flexible tip device 610 and the conductive layer 624 to insulate the conductive layer 624 along the length of the shaft 627 except at the distal or tip portion of the flexible tip device 610 for delivering RF energy. In use, the conductive layer may be use to deliver RF energy during the procedure (e.g., for mapping or ablation) and the non-conductive compliant section 626 serves to insulate the piezoelectric sensors 620a-f.

It is noted that still more piezoelectric sensors in addition to those shown in FIGS. 5 and 5a through FIGS. 10 and 10a may be implemented in other embodiments. Additional piezoelectric sensors may serve to increase the sensitivity of the output. Likewise, the piezoelectric sensors may be positioned relative to one another in any suitable manner and the positioning is not limited to the orientations shown in the figures. The number and positioning of piezoelectric sensors may depend at least to some extent on various design considerations, such as the desired sensitivity, size, and cost of the flexible tip device, as will be readily understood by those having ordinary skill in the art after becoming familiar with the teachings herein.

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. In addition, various combinations of the embodiments shown are also contemplated even if not particularly described. Changes in detail or structure, such as but not limited to combinations of various aspects of the disclosed embodiments, may be made without departing from the spirit of the invention as defined in the appended claims.

What is claimed is:

1. A tissue contact sensing system comprising:
   a plurality of sensors extending in a direction coaxial to a central longitudinal axis of a shaft and offset within a tip of the shaft; and
   a signal processing device electrically connected to the sensors, the signal processing device configured to receive electrical signals from the plurality of sensors which are generated in response to contact stress of the tip, and assesses a direction of tissue contact on the tip based on the received electrical signals.

2. The tissue contact sensing system of claim 1, wherein the sensors are arranged within the tip to detect axial stress.

3. The tissue contact sensing system of claim 1, wherein the sensors are arranged within the tip to detect angular stress.

4. The tissue contact sensing system of claim 1, wherein the sensors are arranged within the tip to detect radial stress.

5. The tissue contact sensing system of claim 1, wherein the sensors are arranged within the tip to detect both axial stress and angular stress.

6. The tissue contact sensing system of claim 1, further comprising an opening formed through a center of the sensors.

7. The tissue contact sensing system of claim 1, wherein the sensors are arranged to provide an irrigation path to irrigated electrodes in the tip.

8. The tissue contact sensing system of claim 1, wherein the sensors are individually insulated.

9. The tissue contact sensing system of claim 1, wherein the sensors are provided in a conductive compliant section.

10. The tissue contact sensing system of claim 1, further comprising a conductive layer surrounding a non-conductive compliant section of the tip.

11. The tissue contact sensing system of claim 1, further comprising a non-conductive shield between the shaft and the tip and a conductive layer.

12. The tissue contact sensing system of claim 11, wherein the non-conductive shield insulates the conductive layer along a length of the shaft except at a distal portion of the tip for delivering radio frequency (RF) energy.

13. The tissue contact sensing system of claim 12, wherein the conductive layer is configured to delivery RF energy.

14. The tissue contact sensing system of claim 13, wherein the non-conductive compliant section is configured to insulate the sensors.

15. A catheter comprising:
    a plurality of sensors extending in a direction coaxial to a central longitudinal axis of a shaft and offset within a tip of the shaft, the plurality of sensors generating electrical signals generated in response to contact stress of the tip for assessing a direction of tissue contact on the tip.

16. The catheter of claim 15, wherein the sensors are arranged within the tip to detect at least one of axial stress, angular stress, and radial stress.

17. The catheter of claim 15, wherein the sensors are individually insulated.

18. The catheter of claim 15, wherein the sensors are provided in a conductive compliant section.

19. The catheter of claim 15, further comprising a conductive layer surrounding a non-conductive compliant section of the tip, and a non-conductive shield between the shaft and the tip and a conductive layer, wherein the non-conductive shield insulates the conductive layer along a length of the shaft except at a distal portion of the tip for delivering radio frequency (RF) energy.

20. A catheter with tissue contact assessment, comprising:
    a conductive layer surrounding a non-conductive compliant section of a tip; and
    a plurality of sensors within the non-conductive compliant section of the tip, the plurality of sensors generating electrical signals generated in response to contact stress of the tip to detect at least one of axial stress, angular stress, and radial stress indicative of a direction of tissue contact on the tip.

* * * * *